United States Patent
Manuel et al.

(10) Patent No.: US 9,795,427 B2
(45) Date of Patent: Oct. 24, 2017

(54) ARTICLES COMPRISING REVERSIBLY ATTACHED SCREWS COMPRISING A BIODEGRADABLE COMPOSITION, METHODS OF MANUFACTURE THEREOF AND USES THEREOF

(71) Applicant: UNIVERSITY OF FLORIDA RESEARCH FOUNDATION, INC., Gainesville, FL (US)

(72) Inventors: Michele Viola Manuel, Gainesville, FL (US); James F. Schumacher, Alpharetta, GA (US); Emily Hester, Orlando, FL (US); Daniella C. van der Merwe, Palm Harbor, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 15/033,182

(22) PCT Filed: Nov. 5, 2014

(86) PCT No.: PCT/US2014/064065
§ 371 (c)(1),
(2) Date: Apr. 29, 2016

(87) PCT Pub. No.: WO2015/069724
PCT Pub. Date: May 14, 2015

(65) Prior Publication Data
US 2016/0270833 A1 Sep. 22, 2016

Related U.S. Application Data

(60) Provisional application No. 61/900,055, filed on Nov. 5, 2013.

(51) Int. Cl.
*A61F 5/00* (2006.01)
*A61B 17/86* (2006.01)
(Continued)

(52) U.S. Cl.
CPC ........ *A61B 17/8605* (2013.01); *A61C 8/0012* (2013.01); *A61C 8/0022* (2013.01);
(Continued)

(58) Field of Classification Search
CPC combination set(s) only.
See application file for complete search history.

(56) References Cited

U.S. PATENT DOCUMENTS 4,713,004 A 12/1987 Linkow
4,791,929 A 12/1988 Jarrett
(Continued)

FOREIGN PATENT DOCUMENTS

| EP | 2014319 A1 | 1/2009 |
| EP | 2022443 B1 | 2/2009 |
| WO | WO2011105685 A2 | 9/2011 |

OTHER PUBLICATIONS

Berglund, Ida S., et al.; "Synthesis and Characterization of Mg-Ca-Sr Alloys for Biodegradable Orthopedic Implant Applications"; Society for Biomaterials; Jun. 12, 2012; pp. 1524-1534.
(Continued)

*Primary Examiner* — Sameh Boles
(74) *Attorney, Agent, or Firm* — Thomas Horstemeyer, LLP

(57) ABSTRACT

Disclosed herein is an article comprising a first screw and a second screw, the first screw being reversibly attached to the second screw such that a longitudinal axis of the first screw coincides with or is parallel to a longitudinal axis of the second screw; the first screw and the second screw each comprising a biodegradable composition, the biodegradable
(Continued)

Figure 3:
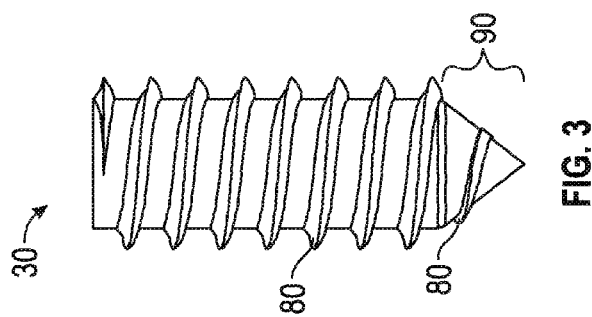

composition comprising a metal or metal alloy comprising magnesium, strontium, zinc, calcium or a combination comprising at least one of the foregoing. Methods of making and using the article are also disclosed herein.

9 Claims, 1 Drawing Sheet

(51) Int. Cl.
  *A61C 8/00* (2006.01)
  *A61F 2/02* (2006.01)
  *A61B 17/00* (2006.01)

(52) U.S. Cl.
  CPC ...... *A61F 2/02* (2013.01); *A61B 2017/00526* (2013.01); *A61C 8/0074* (2013.01); *A61F 2210/0004* (2013.01)

(56) References Cited

U.S. PATENT DOCUMENTS

| | | | |
|---|---|---|---|
| 6,896,517 B1 | 5/2005 | Bjoern | |
| 7,771,774 B2 | 8/2010 | Berckmans, III | |
| 8,197,480 B2 | 6/2012 | Roller et al. | |
| 8,968,002 B2 | 3/2015 | Purga | |
| 2003/0087197 A1 | 5/2003 | Schulman | |
| 2004/0241314 A1 | 12/2004 | Li | |
| 2005/0079200 A1 | 4/2005 | Rathenow | |
| 2005/0250073 A1 | 11/2005 | Tresser | |
| 2005/0266041 A1 | 12/2005 | Gerold et al. | |
| 2006/0106390 A1* | 5/2006 | Jensen | A61B 17/8685 606/318 |
| 2006/0198869 A1 | 9/2006 | Furst et al. | |
| 2008/0118893 A1 | 5/2008 | Armellini | |
| 2008/0243242 A1 | 10/2008 | Kappelt | |
| 2008/0312736 A1 | 12/2008 | Mueller | |
| 2009/0131540 A1 | 5/2009 | Hiromoto | |
| 2009/0226857 A1 | 9/2009 | Grant | |
| 2010/0075162 A1 | 3/2010 | Yang et al. | |
| 2010/0106243 A1 | 4/2010 | Wittchow | |
| 2010/0161031 A1 | 6/2010 | Papirov et al. | |
| 2011/0054629 A1 | 3/2011 | Seok et al. | |
| 2011/0076319 A1 | 3/2011 | Orlowski et al. | |
| 2011/0319986 A1 | 12/2011 | Bayer | |
| 2014/0154341 A1 | 6/2014 | Manuel | |

OTHER PUBLICATIONS

Bornapour, M., et al.; "Biocornpatibility and Biodegradability of Mg-Sr Alloys: The Formation of Sr-Substituted Hydroxyapatite"; Acta Biornaterialia vol. 9 (2013); Aug. 5, 2012; pp. 5319-5330.

Brar, et al. "Investigation of the mechanical and degradation properties of Mg-Sr and Mg-Zn-Sr alloys for use as potential biodegradable implant materials." Journal of the Mechanical Behavior of Biomedical Materials 7 (2012) 87-95.

Brar, H. S. et al. "A study of biodegradable Mg-3Sc-3Y alloy and the effect of surface passivation on in-vitro degradation" Acta Biornaterialia 9 (2013) 5331-5340.

Chen SL, Daniel S, Zhang F, Chang YA, Yan XY, Xie FY, Schmid-Fetzer R, Oates WA. "The PANDAT Software Package and its Applications" CALPHAD 2002; 26: (175-188).

International Preliminary Report on Patentability for Application No. PCT/US2011/042892 Filing Date Jul. 2, 2011; Issue Date Jan. 8, 2013 (6 pages).

International Search Report for Application No. PCT/US2011/042892 Filing Date Jul. 2, 2011; Mailing Date Mar. 20, 2012 (4 pages).

International Search Report for Application No. PCT/US2014/045364 Filing Date Jul. 3, 2014; Mailing Date Oct. 28, 2014 (6 pages).

International Search Report for Application No. PCT/US2014/064065 Filing Date Nov. 5, 2014; Mailing Date Feb. 18, 2015 (8 pages).

Li Z, Gu X, Lou S, Zheng Y. "The development of binary Mg-Ca alloys for use as biodegradable materials within bone" Biomaterials 2007; 29: (1329-1344).

Wan Y, Xiong G, Luo H, He F, Huang Y. Zhou X, "Preparation and characterization of a new biomedical magnesium-calcium alloy" Materials & Design 2008; 29: (2034-2037).

Written Opinion for Application No. PCT/US2011/042892 Filing Date Jul. 2, 2011; Mailing Date Mar. 20, 2012 (5 pages).

Written Opinion for Application No. PCT/US2014/064065 Filing Date Nov. 5, 2014; Mailing Date Feb. 18, 2015 (5 pages).

Written Opinion for International Application No. PCT/US2014/045364 Filing Date Jul. 3, 2014; Mailing Date Oct. 28, 2014 (9 pages).

* cited by examiner

Figure 2:
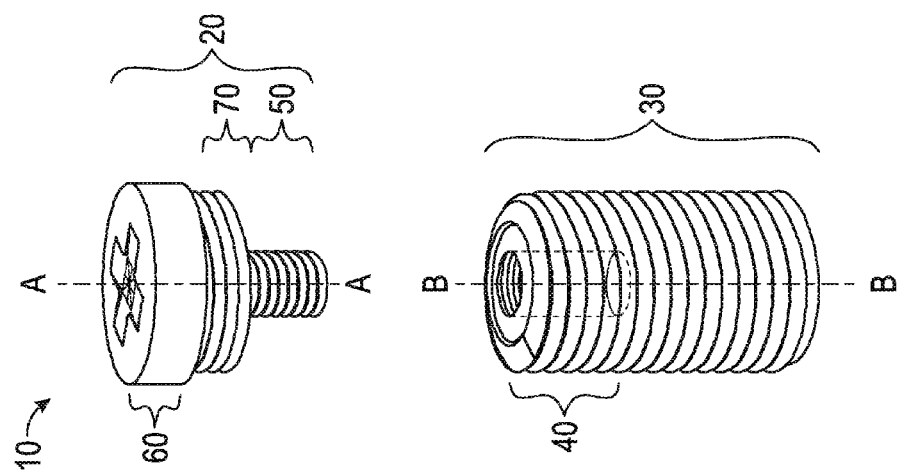
Figure 1:
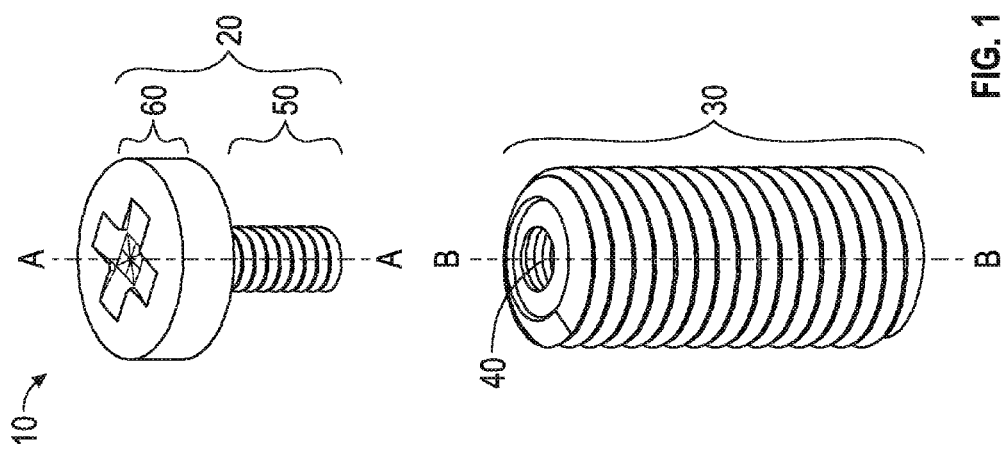

US 9,795,427 B2
                          1                                                          2
ARTICLES COMPRISING REVERSIBLY              composition comprising a metal or metal alloy comprising
ATTACHED SCREWS COMPRISING A                magnesium, strontium, zinc, calcium, or a combination
BIODEGRADABLE COMPOSITION,                  comprising at least one of the foregoing.
METHODS OF MANUFACTURE THEREOF                  Disclosed herein too is a method comprising molding a
AND USES THEREOF                            first screw; and molding a second screw, the first screw
                                            being reversibly attached to the second screw such that a
    CROSS-REFERENCE TO RELATED              longitudinal axis of the first screw coincides with or is
         APPLICATIONS                       parallel to a longitudinal axis of the second screw, wherein
                                            the first and/or second screw comprises a biodegradable
   This application claims priority to International Applica-    composition, which comprises a metal or a metal alloy
tion No. PCT/US14/064065 having a filing date of Nov. 5,    comprising magnesium, strontium, zinc, calcium, or a com-
2014 which claims the benefit of U.S. Application No.       bination comprising at least one of the foregoing.
61/900,055 filed on Nov. 5, 2013, the entire contents of        Disclosed herein too is a method comprising disposing in
which are hereby incorporated by reference.                 the body of a living being an article comprising a first screw;
                                            and a second screw, the first screw being reversibly attached
           BACKGROUND                       to the second screw such that a longitudinal axis of the first
                                            screw coincides with or is parallel to a longitudinal axis of
   This disclosure relates to articles comprising reversibly    the second screw; wherein the first screw and the second
attached screws comprising a biodegradable composition,     screw comprise a biodegradable composition, the biode-
methods of manufacture thereof and uses thereof.            gradable composition comprising a metal or metal alloy
   Orthopedic implants are medical devices which are sur-   comprising magnesium, strontium, zinc, calcium, or a com-
gically implemented in order to repair/support an injury to a    bination comprising at least one of the foregoing.
bone or to replace a damaged bone in a living being.
Implementation of the implant, also known as "internal              BRIEF DESCRIPTION OF DRAWINGS
fixation", anchors the bones in which they are implanted,
thereby facilitating healing of the injury.                     FIG. 1 is a side view of the assembly of a first screw and
   Non-biodegradable implants suffer from various draw-     a second screw in an article according to an embodiment of
backs. Non-biodegradable implants may present biocompat-    the invention;
ibility concerns over time if the implant is not removed from    FIG. 2 is a side view of the assembly of the first screw and
the living being. Non-biodegradable implants may also       the second screw where the first screw has an adaptable
involve a second surgical procedure in order to remove the    head, according to another embodiment of the invention;
implant after healing is complete. Non-biodegradable        and
implants (e.g., titanium implants) may also be significantly    FIG. 3 is a side view of the second screw according to
stronger than the bone in the living being in which they are    another embodiment of the invention.
employed. This difference between the strength of the bone
compared to the relative strength of the implant leads to             DETAILED DESCRIPTION
stress shielding. Stress shielding occurs when the implant
bears bodily stress, rather than sharing the bodily stress with    Disclosed herein is an article (e.g., a medical or dental
the bone, due to the much higher relative strength of the    implant) that comprises a biodegradable composition com-
implant. Stress shielding in turn leads to bone atrophy.    prising a metal or a metal alloy. In an embodiment, the
   Biodegradable orthopedic implants may avoid biocom-      article comprises a first screw and a second screw, the first
patibility issues; however, biodegradable implants which are    screw being reversibly attached to the second screw such
based upon polymers have significantly lower strength than    that a longitudinal axis of the first screw coincides with a
non-biodegradable implants. Such biodegradable implants     longitudinal axis of the second screw. Torque applied to the
also have a high degradation rate and/or degradation is    first screw is transmitted to the second screw to secure parts
incomplete, resulting in an undesirable residual pool. Bio-    of the body (e.g., bones) together. Both screws are then
degradable orthopedic implants are thus limited to low-load    absorbed into the body of a living being without any
implant applications. Biodegradable implants may also       contamination of surrounding tissue or without any adverse
employ specialized equipment, surface pre-treatments and/    effects to the body. In an embodiment, the article comprises
or simplified substrate geometries.                         a non-biodegradable portion and biodegradable portion that
   It is therefore desirable to develop an article which avoids    comprises the biodegradable composition. The biodegrad-
the above-described problems, reduces stress shielding,     able portion may be a coating or may be an integral part of
improves stress sharing, is suitable in high-load applications,    the article.
does not form a residual pool after degradation, is produced    The biodegradable article promotes healing, e.g., bone
without specialized equipment, surface pre-treatments and/    growth, at the implantation site when the article is disposed
or restricted substrate geometries and/or positively influ-    inside the body of a living being. The use of the biodegrad-
ences bone growth and/or the healing process, when the      able composition enhances the biocompatibility of the
article is used in the body of a living being.              article and/or promotes healing following implantation of
                                            the article until the biodegradable composition is eventually
        SUMMARY OF INVENTION                degraded. The biodegradable composition thus provides a
                                            temporary enhancement to the article during a targeted
   Disclosed herein is an article comprising a first screw; and    duration of time following implantation of the article. The
a second screw, the first screw being reversibly attached to    biodegradable composition may also be used to improve the
the second screw such that a longitudinal axis of the first    biocompatibility of electronic circuit components in medical
screw coincides with or is parallel to a longitudinal axis of    devices such as pacemakers.
the second screw; the first screw and the second screw each    Disclosed herein too is a method comprising molding a
comprising a biodegradable composition, the biodegradable    first screw and molding a second screw. The first screw is reversibly attached to the second screw such that a longitudinal axis of the first screw coincides with or is parallel to a longitudinal axis of the second screw, wherein the first and/or second screw comprises the biodegradable composition. Disclosed herein too is a method comprising disposing the article described herein in the body of a living being.

Referring to FIG. 1, the article 10 comprises a first screw 20 and a second screw 30, the first screw 20 being reversibly attached to the second screw 30 such that a longitudinal axis A-B of the first screw 20 coincides with a longitudinal axis A-B of the second screw 30. The longitudinal axis A-B extends longitudinally along the length of the first screw 20 and the second screw 30, respectively. As may be seen by reference to FIG. 1, the first screw 20 is concentrically disposed in the second screw 30, i.e., a longitudinal axis of the first screw 20 coincides with the longitudinal axis of the second screw 30. In an embodiment, the first screw 20 is eccentrically disposed in the second screw 30, i.e., a longitudinal axis of the first screw 20 is parallel to the second screw 30, but not coincident with it. The second screw 30 has a threaded hole 40 which is of sufficient size to accommodate the first screw 20. The first screw 20 further comprises a first screw shaft 50 and a screw head 60. The screw head 60 is adapted to be screwed into the second screw 30 using a tool (e.g., a screwdriver) which is complimentary to the shape of the screw head 60. The second screw 30 does not have a screw head, but has threads in the threaded hole 40 that are adapted to receive the first screw 20.

In an embodiment, the longitudinal axis of the first screw 20 is parallel to the longitudinal axis of the second screw 30. In yet another embodiment, the longitudinal axis of the first screw 20 is inclined at an angle other than 0° relative to the longitudinal axis of the second screw 30.

In an embodiment, the ratio of the (outer) diameter of the first screw shaft 450 to the (outer) diameter of the second screw 30 is 1:2 to 1:10.

In an embodiment, the length of the first screw shaft 50 is equal to or less than one-half, specifically equal to or less than one-third, and more specifically equal to or less than one-quarter of the length of the second screw 30.

Referring to FIG. 1, the first screw shaft 50 and the second screw 30 are each threaded. The second screw 30 is threaded in a manner to accommodate the threading on the first screw shaft 50. The second screw 30 is also threaded. The thread pitch is selected such that the threads have a relatively thick profile while maintaining a minimal surface area. The thread pitch is also selected such that degradation rate of the traders in comparison to the overall article is not adversely affected.

Various types of threads may be employed. Non-limiting examples of such threads include left-handed threads and right-handed threads. In an embodiment, the threads on both of the first screw shaft 50 and the second screw 30 are either right-handed or left-handed threads so that the first screw shaft 50 will become fixed into the second screw 30 while the first screw 20 is tightened into place within the second screw 30.

Referring to FIG. 2, in an embodiment, the first screw 20 further comprises an adaptable screw head 60. The adaptable screw head 60 is adapted to accommodate a secondary screw head 70 by combining the secondary screw head 70 with the first screw shaft 50, which allows the design of the screw head to be made compatible with existing screw head products. Alternatively, the first screw 20 and/or the article 10 is adapted to interface with a bone plate (not shown).

Referring to FIG. 3, in an embodiment, the second screw 30 has a conically shaped end 90 opposite the end that is in contact with the first screw 20. The conically shaped end 90 is also threaded. The conically shaped end 90 of the second screw 30 assists with implementation of the article 10 in a living being during a self-tapping process.

In an embodiment, the article 10 can be molded entirely from the biodegradable composition, and hence is wholly biodegradable. In another embodiment, the article 10 comprises and/or is molded from a non-biodegradable composition, and hence is partially biodegradable. In yet another embodiment, the biodegradable composition is at least one coating applied to at least a portion of the first and/or second screw.

The biodegradable composition comprises a metal or a metal alloy, where the metal or metal alloy comprises calcium, strontium, zinc, magnesium or a combination comprising at least one of the foregoing. In an embodiment, the metal alloy comprises two or more elements where at least one element is calcium, strontium, zinc or magnesium.

In yet another embodiment, the metal alloy comprises 3 or more elements (i.e., it is a ternary alloy). In one embodiment, the metal alloy comprises 4 or more elements. In another embodiment, the metal alloy comprises 5 or more elements. In an exemplary embodiment, the metal alloy comprises of 3 or more elements. The metal alloy comprises a base metal, a second element and a third element. The metal alloy has the formula (1) shown below:

$$M_x M_y M_z \qquad (1)$$

where $M_x$ is a base metal, $M_y$ is a second element and $M_z$ is a third element, where x, y and z represent the weight fractions of the respective metals in the metal alloy and where the sum of x, y and z is equal to 100% (if measured in terms of a percentage) or 1 (if measured in terms of a fraction). For example, if the base metal constitutes 70 weight percent (wt %) of the metal alloy, the second element constitutes 20 wt % of the metal alloy and the third element constitutes 10 wt % of the metal alloy, then x=0.7, y=0.2 and z=0.1 and the sum of x, y and z=1 or x=70%, y=20% and z=10% and the sum of x, y and z=100%. It is to be noted that the second and the third elements are metals.

The base metal is that metal that is present in the metal alloy in the largest amount. The base metal comprises magnesium, calcium, zinc, strontium, or a combination comprising at least one of the foregoing base metals. The base metal is present in the metal alloy in an amount of about 40 to about 99 wt %, specifically about 50 to 98 wt %, and more specifically about 60 to about 97 wt %, based on the total weight of the metal alloy. An exemplary base metal is magnesium.

The second element and the third element are different in composition from each other and are selected from the group consisting of scandium, yttrium, gadolinium, cerium neodymium, dysprosium, or a combination thereof.

The second element is present in an amount of about 0.5 to about 40 wt %, specifically about 0.5 to 20 wt %, and more specifically about 1.0 to about 5 wt %, based on the total weight of the metal alloy. In an exemplary embodiment, the second element is scandium.

The third element is present in an amount of about 0.1 to about 20 wt %, specifically about 1 to about 8 wt %, and more specifically about 1.5 to about 4 wt %, based on the total weight of the metal alloy. In an exemplary embodiment, the third element is yttrium.

The weight ratio of the second element to the third element is about 0.2:1 to about 1:0.25, specifically about 0.5:1 to about 1:0.5, and more specifically about 0.75:1 to 1:0.75.

Minor amounts of other elements may be added to the metal alloy to refine the structure. Examples of such elements are manganese and zirconium. These elements are added in amounts of 0.1 to about 1 wt %, based on the total weight of the alloy.

In one embodiment, when magnesium is used as the base metal, scandium is used as the second element and yttrium is used as the third element. The magnesium is used in amounts of about 92 to about 96 wt %, while scandium is used in amounts of about 1.5 to about 4.0 wt %, while yttrium is used in amounts of about 1.5 to about 4.0 wt %.

The article 10 may further comprise additional elements commonly used with medical or dental implants, including, but not limited to pins, rods and/or plates. These additional elements may similarly be wholly or partially composed of the biodegradable composition, or may not include the biodegradable composition at all.

In an embodiment, at least a portion of the article 10 is coated with a plurality of nanoparticles, the plurality of nanoparticles comprising a medical treatment composition. In another embodiment, the plurality of nanoparticles have a hollow core in which the medical treatment composition is disposed and the plurality of nanoparticles are at least partially coated with the biodegradable coating composition. The plurality of nanoparticles thus facilitate the time-released, and/or targeted delivery of the medical treatment composition.

In an embodiment, the nanoparticles in the plurality of nanoparticles are randomly distributed in a coating on the article 10. In an embodiment, the nanoparticles in the plurality of nanoparticles are uniformly distributed in a coating on the article 10.

Any type or size of nanoparticle may be employed. Non-limiting examples of nanoparticles include, nanotubes, nanospheres, nanowires, and the like, or a combination comprising at least one of the foregoing. In an embodiment, the plurality of nanoparticles have an average particle size of 1 to 10,000 nm, specifically, 1 to 1,000 nm, more specifically 1 to 100 nm.

In an embodiment, in one method of manufacture, the first screw 20 and/or the second screw 30 is molded. Any suitable molding technique may be employed to mold the first screw 20 and/or the second screw 30. Non-limiting examples of molding techniques include injection molding and compression molding, In another embodiment, the first screw 20 and/or the second screw 30 is machined (e.g., using a lathe).

The article 10 is high-load-bearing. In an embodiment, the article is capable of withstanding loads of up to 200 kg, specifically up to 180 kg, more specifically up to 160 kg, and even more specifically up to 140 kg.

The article 10 has a strength which is substantially similar to that of a bone in a living being in comparison to a titanium implant. In an embodiment, the article 10 has a modulus of elasticity of at least 80 GPa, specifically at least 60 GPa, more specifically 50 GPa, and even more specifically at least 40 GPa.

The article may be employed as an orthopedic implant (e.g., a medical or a dental implant) when disposed inside a living being. The article 10 is thus capable of bearing high loads, reduces stress shielding, improves stress sharing, does not form a residual pool after degradation, is produced without specialized equipment, surface pre-treatments and/or restricted substrate geometries and/or positively influences bone growth and/or the healing process, when the article is used in the body of a living being.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. An article comprising: a first screw; and a second screw, the first screw being reversibly attached to the second screw such that a longitudinal axis of the first screw coincides with or is parallel to a longitudinal axis of the second screw; where at least one of the first screw or the second screw comprises a biodegradable composition, the biodegradable composition comprising a metal or metal alloy comprising magnesium, strontium, zinc, calcium, or a combination comprising at least one of the foregoing, wherein at least a portion of the article is coated with a plurality of nanoparticles, the plurality of nanoparticles comprising a medical treatment composition.

2. The article of claim 1, wherein the article is wholly biodegradable.

3. The article of claim 1, wherein the article comprises a biodegradable portion and a non-biodegradable portion.

4. The article of claim 1, wherein at least a portion of the article is coated with the biodegradable composition.

5. The article of claim 1, wherein the article is self-tapping.

6. The article of claim 1, wherein the first screw has a first screw head which is adapted to accommodate a second screw head.

7. The article of claim 1, wherein the first screw comprises a first screw shaft and the ratio of the diameter of the first screw shaft to the outer diameter of the second screw is 0.5 to 0.8.

8. The article of claim 1, wherein the base metal is present in an amount of from 60 to 97 wt %.

9. The article of claim 1, wherein the article is an implant in the body of a living being.

* * * * *